United States Patent
Balgley (10) Patent No.: US 9,372,196 B2
(45) Date of Patent: Jun. 21, 2016

(54) FORMALIN-FIXED ISOTOPE-LABELED REFERENCE STANDARDS AND METHODS FOR FABRICATION AND USE THEREOF

(75) Inventor: Brian M. Balgley, Fairfax Station, VA (US)

(73) Assignee: BIOPROXIMITY, LLC, Springfield, VA (US)

( * ) Notice: Subject to any disclaimer, the term of this patent is extended or adjusted under 35 U.S.C. 154(b) by 582 days.

(21) Appl. No.: 13/413,110

(22) Filed: Mar. 6, 2012

(65) Prior Publication Data

US 2012/0231469 A1 Sep. 13, 2012

Related U.S. Application Data

(60) Provisional application No. 61/450,399, filed on Mar. 8, 2011.

(51) Int. Cl.
| | | |
|---|---|---|
| *G01N 1/30* | (2006.01) | |
| *G01N 33/68* | (2006.01) | |
| *C12N 5/00* | (2006.01) | |

(52) U.S. Cl.
CPC ........ *G01N 33/6842* (2013.01); *G01N 33/6848* (2013.01); *C12N 5/00* (2013.01); *G01N 2496/00* (2013.01); *G01N 2570/00* (2013.01)

(58) Field of Classification Search
USPC .......................................... 435/40.5; 250/282
See application file for complete search history.

(56) References Cited

U.S. PATENT DOCUMENTS

| | | | |
|---|---|---|---|
| 5,610,022 A | 3/1997 | Battifora | |
| 6,746,848 B2 | 6/2004 | Smith | |
| 7,125,685 B2 * | 10/2006 | Chen ................................ | 435/23 |
| 7,473,532 B2 | 1/2009 | Darfler et al. | |
| 7,588,890 B2 | 9/2009 | Chu | |
| 8,026,084 B2 * | 9/2011 | Ecker et al. ................... | 435/91.2 |
| 2006/0127956 A1 | 6/2006 | Sompuram et al. | |
| 2009/0136971 A1 * | 5/2009 | Krizman et al. ............. | 435/7.92 |
| 2010/0086948 A1 * | 4/2010 | Gold et al. .................... | 435/7.21 |
| 2010/0255531 A1 * | 10/2010 | Deininger ..................... | 435/40.5 |
| 2011/0062320 A1 * | 3/2011 | Pevsner et al. ................ | 250/282 |

OTHER PUBLICATIONS

Huang, Wei et al. Raman-FISH: combining stable-isotope Raman spectroscopy and fluorescence in situ hybridization for the single cell analysis of identity and function. Environmental Microbiology (2007) 9(8), pp. 1878-1889.*

Guerrero, Cortnie et al. An Integrated Mass Spectrometry-based Proteomic Approach. Published by Molecular & Cellular Proteomics Papers in Press, Nov. 11, 2005. pp. 366-378.*

Ostasiewicz, Pawel et al. Proteome, Phosphoproteome, and N-Glycoproteome Are Quantitatively Preserved in Formalin-Fixed Paraffin-Embedded Tissue and Analyzable by High-Resolution Mass Spectrometry. Journal of Proteome Research 2010. pp. 3688-3700.*

Hood, Brian et al. Unravelling the proteome of formalin-fixed paraffin-embedded tissue. Briefings in Functional Genomics and Proteomics. vol. 5. No. 2. 169-175. publication date May 10, 2006.*

Hood, Brian. Mass spectrometric analysis of formalin-fixed paraffin-embedded tissue: Unlocking the proteome within. Proteomics 2006, 6, pp. 4106-4114.*

Geiger et al., "Super-SILAC Mix for Quantitative Proteomics of Human Tumor Tissue," *Nature Methods*, May 2010, 7(5): pp. 383-385.

Geiger et al., "Use of Stable Istope Labeling by Amino Acids in Cell Culture as a Spike-in Standard in Quantitative Proteomics," *Nature Protocols*, 2011, (abstract only) HubMed [online]. [retrieved on Mar. 6, 2012]. Retrieved from the Internet: <URL: http://www.hubmed.org/display.cgi?uids=21293456>.

Ong et al., "Stable Isotope Labeling by Amino Acids in Cell Culture for Quantitative Proteomics," Cell Biology [online], 2006 [retrieved on Mar. 6, 2012]. Retrieved from the Internet: <URL: http://digitus.itk.ppke.hu/~cseri/edu/Books/Cell%20Biology/Volume%204/Part%20D/Chapter54.pdf>.

Ong et al., "Stable Isotope Labeling by Amino Acids in Cell Culture, SILAC, as a Simple and Accurate Approach to Expression Proteomics," *Molecular & Cellular Proteomics*, 2002, 1: pp. 376-386.

Rhodes et al., "A Formalin-fixed, Paraffin-processed Cell line Standard for Quality Control of Immunohistochemical Assay of HER-2/neu Expression in Breast Cancer," *American Journal of Clinical Pathology*, Jan. 2002, 117(1): pp. 81-89.

Guo et al., "Rapid mass spectrometric conversion of tissue biopsy samples into permanent quantitative digital proteome maps," *Nature Medicine*, Mar. 2015 [advance online publication], pp. 1-9.

* cited by examiner

*Primary Examiner* — Nghi Nguyen
(74) *Attorney, Agent, or Firm* — Shapiro, Gabor and Rosenberger, PLLC (57) ABSTRACT

One or more cells are labeled with minor stable isotopes, characterized, and preserved for subsequent use as a biospecimen reference standard. The one or more cells are grown in culture media supplied with minor stable isotopes in concentrations substantially different from normally occurring concentrations, thereby supplanting major stable isotopes that would normally be incorporated into the proteins of the cells. The proteins of the cells are thus labeled by the minor stable isotopes and can be used in proteomic characterization of the cells. The cells are preserved by fixation as a reference standard. Cells of the reference standard are mixed with the sample and subject to mass spectrometry evaluation, whereby the labeled proteins of the reference standard can be used in determining the proteome of the sample.

22 Claims, 3 Drawing Sheets

FORMALIN-FIXED ISOTOPE-LABELED REFERENCE STANDARDS AND METHODS FOR FABRICATION AND USE THEREOF

CROSS-REFERENCE TO RELATED APPLICATIONS

The present application claims the benefit of U.S. Provisional Application No. 61/450,399, filed Mar. 8, 2011, which is incorporated by reference herein in its entirety.

FIELD

The present disclosure relates generally to bio-specimen reference standards, and, more particularly, to minor-stable-isotope-labeled bio-specimen reference standards and methods for fabrication and use thereof.

SUMMARY

One or more cells can be labeled with stable isotopes (e.g., minor stable isotopes), can be characterized, and can be preserved for subsequent use as a bio-specimen reference standard, for example, for pathology or other applications. The one or more cells can be grown in culture media supplied with minor stable isotopes in concentrations substantially different from normally occurring concentrations, thereby supplanting major stable isotopes that would normally be incorporated into the proteins of the cells. The proteins of the cells are thus labeled by the minor stable isotopes and can be used in proteomic characterization of the cells. The cells can undergo fixation (e.g., using formalin) to preserve the cells for later comparison with a tissue or cell sample. The cells of the reference standard can be mixed with the sample and subject to mass spectrometry evaluation, whereby the labeled proteins of the reference standard can be used in determining the proteome of the sample.

In embodiments, a bio-specimen reference standard method can include growing one or more cell lines in a medium containing a minor stable isotope therein such that proteins of the one or more cell lines are labeled with said minor isotope. The method can further include characterizing a proteome of the one or more cell lines using the isotope-labeled proteins, and preserving the one or more cell lines by fixation so as to form a bio-specimen reference standard.

In embodiments, a method of using bio-specimen reference standard can include performing a pathological comparison of a sample with the reference standard. A portion of the sample can be combined with a portion of the reference standard. A proteome of the sample can be determined by performing mass spectrometry on the combined portions of the sample and the reference standard. The reference standard can include one or more cells lines preserved by a fixation process. Proteins of the one or more cell lines can be labeled by a minor stable isotope (such as, but not limited to, $^{15}N$ or $^{13}C$) such that an amount of the minor isotope in said proteins is greater than an amount of a respective major isotope. The labeled proteins can be used in determining the proteome of the sample.

In embodiments, a bio-specimen reference standard for use in pathological evaluation of a sample can include one or more cell lines preserved by fixation. The one or more cell lines can have proteins labeled by a minor stable isotope. An amount of the minor stable isotope in the proteins can be greater than an amount of a respective major stable isotope in the proteins. The bio-specimen reference standard can take the form of an array or micro-array, with different cell lines and/or dilutions being spotted at different locations on a common substrate. Alternatively or additionally, the bio-specimen reference standard can take the form of a protein array or micro-array, with the lysates of different cell lines and/or dilutions being spotted at different locations on a common substrate.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described with reference to the accompanying drawings, which have not necessarily been drawn to scale. Where applicable, some features have not been illustrated to assist in the illustration and description of underlying features. Throughout the figures, like reference numerals denote like elements.

DETAILED DESCRIPTION

Embodiments of the disclosed subject matter relate to a bio-specimen that can be used in subsequent analysis and/or assays as a reference standard. In general, embodiments can include one or more cell cultures, at least one of which has been grown in a media containing at least one minor stable isotope. As used herein, major isotope refers to one of the stable isotopes of an element that is the most common on Earth, i.e., the predominant isotope of the element. Minor isotope refers to one of the stable isotopes of an element that occurs less frequently than the major isotope. For example, carbon (C) has naturally occurring isotopes of $^{12}C$, $^{13}C$, and $^{14}C$. However, $^{14}C$ is radioactive and is therefore not considered stable. Of the stable isotopes of carbon, 99% exists as $^{12}C$ while the remaining 1% exists as $^{13}C$. Accordingly, $^{12}C$ is the major stable isotope while $^{13}C$ is the minor stable isotope. Embodiments discussed herein relate to the use of the minor stable isotope for labeling, although in some circumstances it may be possible to label with a major stable isotope.

The growth media can include the minor stable isotope at concentrations greater than its occurrence in nature. For example, the minor stable isotope concentration in the growth media can be equal to or exceed the major stable isotope concentration therein. The minor stable isotope in the media can thus be incorporated into the cell culture, in effect labeling certain portions of the cell culture (e.g., labeling an amino acid or a metabolite). As used herein, labeling using a minor stable isotope refers to incorporating a minor stable isotope into components of the cells (e.g., proteins and/or metabolites) at concentrations greater than the natural occurrence of the minor stable isotope. Thus, for example, if using $^{13}C$ for labeling, the components should incorporate the $^{13}C$ such that greater than 1% of the carbon in these components is $^{13}$C. In one or more embodiments, the labeling may be such that the amount of minor stable isotopes incorporated into the cellular components of the reference standard exceeds the amount of major stable isotopes (e.g., at least 50% or greater, of the carbon in these components, for example, 90%, is in the form of $^{13}$C).

The one or more cell cultures can optionally undergo a desired manipulation, which can include, but is not limited to, enrichment of a subset of the protein constituents (e.g., membrane proteins, phosphoproteins, glycosylated proteins, proteins of different size or charge) and subcellular fractionation (e.g., via sucrose density gradient centrifugation) to enrich for different organelles. Subsequently, the one or more cell cultures can be preserved using a preservative or fixative, such as, but not limited to, formalin. Preservation allows the cultures to retain their morphology without degradation and stably preserves the proteins in the cultures or derivatives for years (e.g., decades). In particular, protein modifications and protein tertiary and quaternary structure, notably protein interactions with cellular constituents (e.g., other proteins, nucleic acids, and/or metabolites) can be maintained almost indefinitely.

Prior to or after fixation, cell cultures or derivatives can be characterized for use in subsequent analyses or assays. For example, the composition of the formalin-fixed bio-specimen can be characterized using mass spectrometry-based proteomics in order to ascertain the protein constituents of the bio-specimen. The characterized bio-specimen can be used as a reference standard to accompany, for example, immunohistochemistry (IHC), immunofluorescence (IF), hemotoxylin and eosin (H&E) stains and/or mass spectrometry-based protein assays. Accordingly, the characterized bio-specimen may be useful for diagnostic and/or pathologic purposes, among other uses.

In embodiments, the bio-specimen can be characterized by mass-spectrometry based proteomics to determine the protein constituents of the bio-specimen. Intact proteins or proteolytic cleavage products of proteins in the bio-specimen standard can be absolutely quantified using known quantities of unlabeled, recombinant proteins or unlabeled, synthetic peptides. Alternatively or additionally, the intact proteins or cleavage products in the bio-specimen standard can be relatively quantified using techniques such as spectral counting, peak area measurements, and derivatives thereof.

Since the bio-specimen is preserved, such as by formalin fixation, the minor stable isotope labeled components of the bio-specimen may serve as a reference for analyses or assays conducted on similarly preserved cellular or tissue samples whose constituents include these same components in an unlabeled state, i.e., the natural state incorporating primarily major stable isotopes. For example, formalin-fixed bio-specimens according to the disclosed embodiments can be used as a reference standard for comparison with and/or characterization of formalin-fixed tissue samples from a patient for disease diagnosis. Because the bio-specimen standard and the tissue sample are similarly preserved, a comparison of the results of assays performed on the standard and the sample may be more informative than if the standard and the sample had been preserved in different manners.

Figure 1:
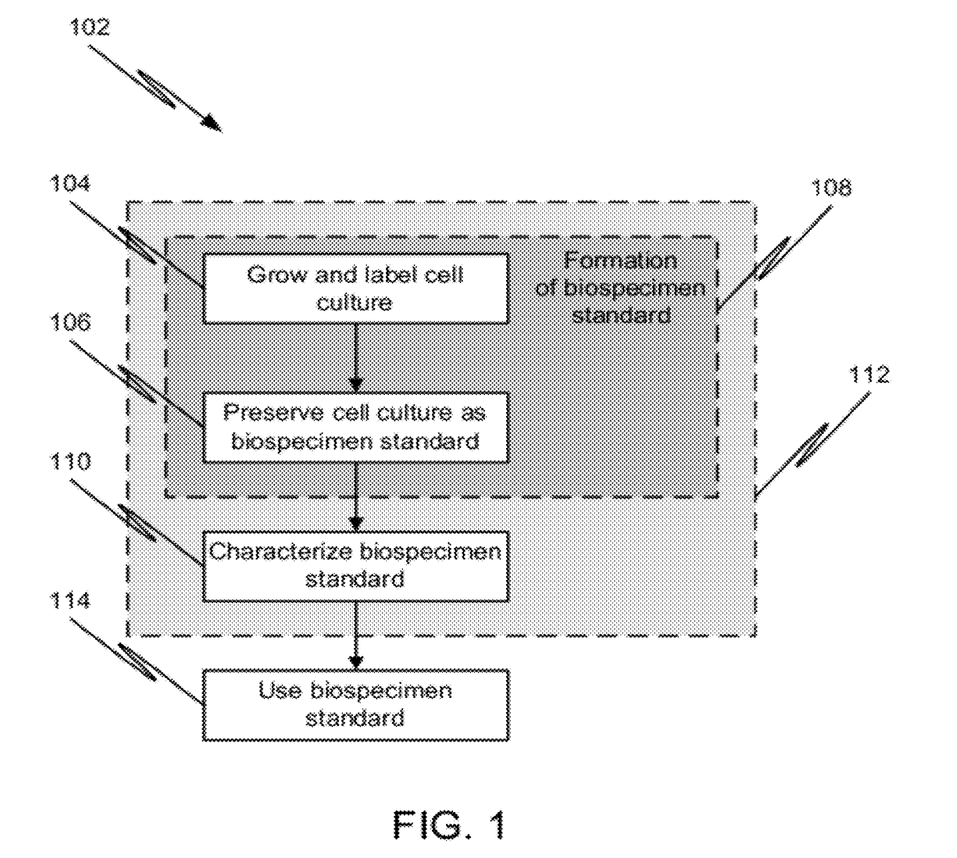
FIG. 1 is a process flow diagram related to the fabrication and use of an isotope-labeled bio-specimen reference standard, according to one or more embodiments of the disclosed subject matter.

With reference to FIG. 1, a diagram is shown illustrating a process 102 for fabricating and/or using a reference standard, according to one or more embodiments of the disclosed subject matter. At 104, a cell culture may be grown in a media having one or more minor stable isotopes therein. For example, the minor stable isotope may be an isotope of a primary element, such as nitrogen or carbon, for example $^{15}$N or $^{13}$C. Note that the major stable isotopes for these primary elements are $^{14}$N and $^{12}$C, respectively. Additionally or alternatively, the minor stable isotopes can be incorporated into one or more molecules. For example, the cell culture can be grown and labeled using a stable isotope labeling by amino acid in cell culture (SILAC) technique.

In SILAC, cell cultures can be prepared in a light cell culture media and heavy cell culture media. The heavy cell culture media can include, for example, a minor stable isotope labeled amino acid or amino acids in place of naturally-occurring, unlabeled forms of that amino acid or those amino acids (i.e., containing the elements according to the natural occurrence of the respective isotopes). For the purposes of preparing a bio-specimen standard as disclosed herein, it is sufficient to prepare the cell culture in only the heavy cell culture media.

Figure 2:
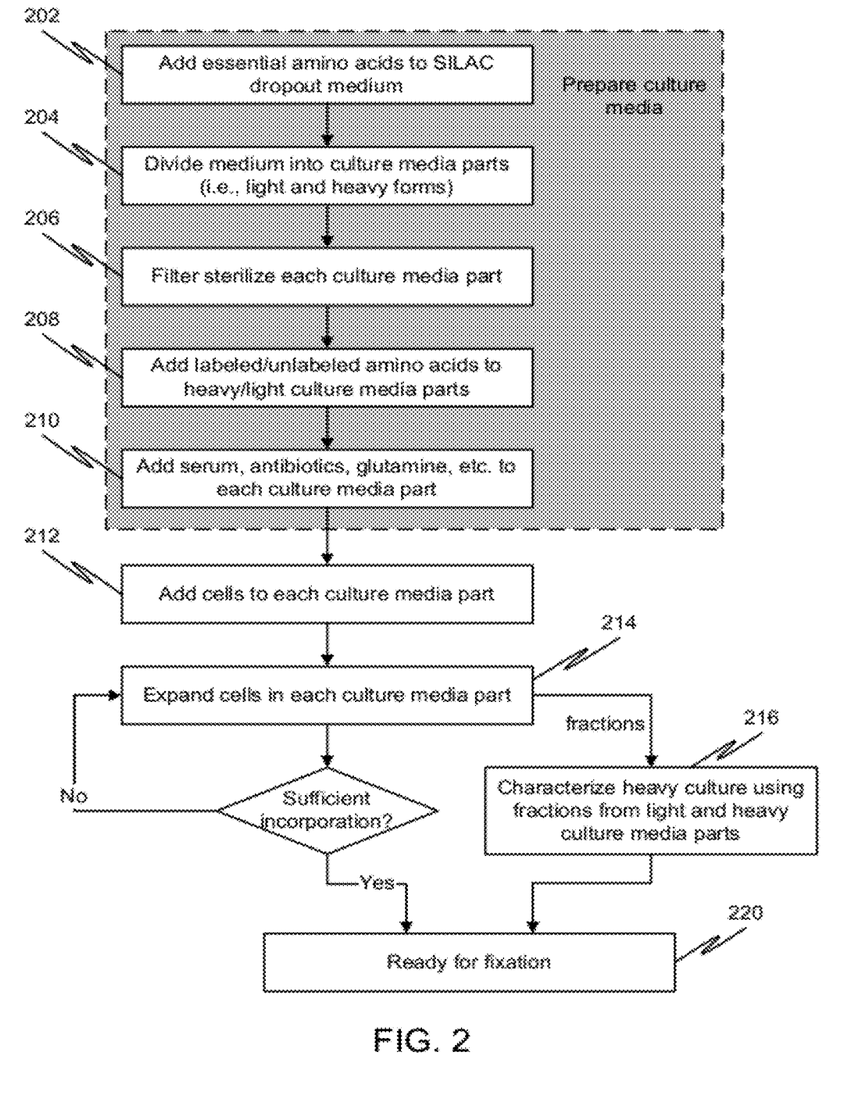
FIG. 2 is a process flow diagram of a SILAC technique, according to one or more embodiments of the disclosed subject matter.

Referring to FIG. 2, a technique for preparing a bio-specimen standard using SILAC is shown. Of course, one or more other methods for preparing the bio-specimen standard with labeled constituents are also possible according to one or more contemplated embodiments. The steps illustrated in FIGS. 1-2 and discussed herein should therefore be understood as exemplary in nature and not limiting of the disclosed subject matter.

At 202, all essential amino acids (unlabeled), with the exception of the heavy amino acid(s) to be used for labeling, can be added to a SILAC dropout medium. If preparing both light and heavy forms of the cell culture media, the medium from 202 can be divided into two equal parts at 204. At 206, each media can be filter sterilized. At 208, the remaining amino acid(s) to be used as labels can then be added to each culture media. For example, $^{13}C_6^{15}N_4$ arginine and/or $^{13}C_6^{15}N_2$ lysine (i.e., minor stable isotope versions) can be added to the heavy preparation while the natural/unlabeled $^{12}C_6^{14}N_4$ arginine and/or $^{12}C_6^{14}N_2$ lysine (i.e., major stable isotope versions) can be added to the light preparation. At 210, dialyzed fetal bovine serum, antibiotics and glutamine can be added to each culture media. Additional or substitute components can be added at 210 consistent with standard cell culture practice. It may be preferable to use dialyzed serum so as to prevent, or at least reduce the possibility of, contamination of the cell cultures with amino acids from the serum.

At 212, cells, which have been grown in standard culture media (e.g., HeLa cells growing in Dulbecco's Modified Eagle Medium (DMEM)) at up to 90% confluency, can be split into two separate cultures. One of these cultures can then be grown in light medium and the other in the heavy medium, using about 10% of the cells from the original culture. At 214, the cells and subculture can be expanded. For example, the cells and subculture can be expanded for at least five (5) doublings so as to permit adequate incorporation of labeled amino acids. At any point in the process after 212, a small fraction of cells can be taken from the heavy culture and prepared for characterization at 216, for example, by shotgun proteomic measurement so as to measure incorporation of heavy amino acid(s) in the cells. Additional doublings can be undertaken to improve incorporation rates, if necessary or desirable.

At 220, the heavy labeled cell culture is ready for fixation and processing into a bio-specimen standard. Additional bio-specimen standards can be made by this same method. Also, standards can be made using additional and/or different stable isotope labeled amino acids than those listed above, e.g., heavy arginine only, or heavy arginine and heavy lysine, or heavy lysine only, etc. Heavy arginine and heavy lysine can be composed of $^{13}$C and/or $^{15}$N, for example, $^{13}C_6$ arginine, $^{15}N_4$ arginine, $^{13}C_6^{15}N_4$ arginine, $^{13}C_6$ lysine, $^{15}N_2$ sine or $^{13}C_6^{15}N_2$ lysine. Other stable isotope labeled amino acids can also be used in combination with or in substitution of the exemplary heavy amino acids specifically disclosed herein. This results in labeled proteins with masses distinct from other preparations. In this manner it is possible to prepare mixed standards having individually prepared bio-specimen standards, each incorporating a distinct minor stable isotope labeled amino acid or distinct combination of minor stable isotope labeled amino acids.

Referring again to FIG. 1, at 104, more than one cell culture (i.e., cells from more than one cell line, cell type, or tissue type) can be grown in separate media having the stable isotope therein. In addition, one or more stable isotopes can be used for either a single cell culture or multiple cell cultures. The multiple cell cultures can be combined together (e.g., by mixing) into a single bio-specimen for use in the standard. Alternatively, the multiple cell cultures can be maintained separately until after preservation in 106, described below. In still another alternative, the multiple cell cultures can be maintained as separate bio-specimens for subsequent use in 114, described below.

In some embodiments, certain proteins and/or peptides that may be of interest to a particular end user may be lacking from the cell lines employed for the reference standard. The bio-specimen for the reference standard can thus be supplemented or spiked with the desired proteins and/or peptides. Such desired proteins and/or peptides can additionally be labeled using a minor stable isotope, for example, using standard peptide synthesis methods or standard recombinant DNA methods for producing proteins. Alternatively, the cell culture for the reference standard bio-specimen can be grown without any minor isotope labeling while the spiked proteins and/or peptides are minor isotope labeled. In such a standard, the spiked proteins and/or peptides can be the only components that are minor isotope labeled.

Proceeding to 106, the one or more cell cultures can be preserved for subsequent use as a reference standard. In one or more embodiments, preservation can be accomplished by formalin fixation, for example, by incubating cells, tissues or fluids in formalin, which is a solution of formaldehyde, at any concentration, in water and in some cases other components. Tissues are often fixed in 10% neutral buffered formalin, the composition of which may vary based on the manufacturer. For example, a preparation of formalin can include formaldehyde diluted to 10% concentration in a phosphate buffered saline solution (PBS). Formaldehyde can be diluted to differing concentrations to modulate the fixation process. Other buffers can be substituted for PBS to accommodate differing protocols. Also, paraformaldehyde or glutaraldehyde can be partially or fully substituted for formaldehyde.

Chemical agents can be used to modulate the formaldehyde fixation process. For example, glycine can be used to quench the cross-linking process, and/or various inhibitors, such as protease or phosphatase inhibitors, can be used to slow biological reactions. Other processes can also be used to modulate the fixation process. For example, the process can be performed at 4° C. to slow biological reactions. In another example, the process can be performed at elevated temperatures to speed the cross-linking reaction. Additionally or alternatively, the process can be performed in the presence of ultrasound modulation and/or under elevated pressures to increase the rate of the process. Other processes and variations for fixation than those disclosed herein are also possible according to one or more contemplated embodiments. The fixation processes are thus not limited to the examples explicitly disclosed herein.

In embodiments, the preservation techniques can be substantially similar to those preservation techniques applied to tissue samples acquired from a patient, for example, for disease diagnosis. Thus, the resulting bio-specimen standard can be preserved in a substantially similar form as the tissue sample it will be compared to. The growth 104 of the cell culture together with the preservation of the cell culture 106 can serve as substeps of an overall formation 108 of the bio-specimen standard.

In certain embodiments, other formalin fixation protocols can be employed to achieve preservation of the one or more cell cultures. For example, fixative times can be varied, fixative temperatures can be varied, derivatives of formalin can be used, and/or other processing steps can be added according to one or more contemplated embodiments. Additional processing steps can include, but are not limited to, sonication and/or application of increased pressure of the one or more cell cultures during fixation. In certain embodiments, other types of fixatives can be used in place of, or in addition to, formalin. For example, glutaraldehyde can be used.

At 110, the preserved bio-specimen standard can be characterized by one or more assays and/or techniques for subsequent use in 114 as a reference standard. The formation step 108 of the bio-specimen standard together with the characterization 110 can serve as substeps of an overall formation/characterization 112 of the bio-specimen standard. In embodiments, mass spectrometry-based proteomics can be used to characterize the protein constituents of the bio-specimen standard. Such characterization can then later be used in 114 to determine the protein constituents of a sample, for example. Other techniques for characterizing the protein composition of the bio-specimen standard are also possible, for example, H&E stain, IHC and IF.

In addition, morphology of the bio-specimen standard may be helpful in determining particular characteristics of the sample. An end user can image the bio-specimen standard at a same time as the sample, as described below. However, in embodiments, the bio-specimen standard can be imaged during the characterization in 110. For example, one or more images of the standard can be obtained at one or more magnifications and/or using different imaging devices, such as, but not limited to, a light microscope, confocal microscope, multi-spectral microscope, fluorescence microscope, and an electron microscope. The resulting one or more images can be provided along with the bio-specimen standard and the protein characterization data for subsequent evaluation of a sample in 114.

Figure 3:
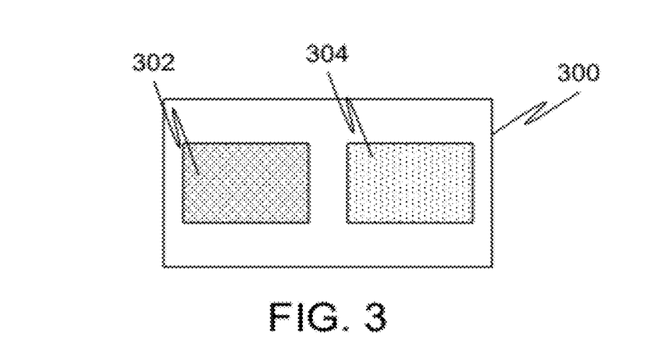
FIG. 3 is a simplified drawing of a plan view of a bio-specimen standard array, according to one or more embodiments of the disclosed subject matter.

Because of the characterization in 110, the bio-specimen standard can serve as a reference point for subsequent evaluation of samples in 114. In general, one or more of the bio-specimen standards can be compared to one or more samples and/or used in assays with the sample to determine one or more characteristics of the sample. In an embodiment, the bio-specimen standard can be visually compared to a sample using, for example, light microscopy to ascertain certain morphological characteristics of the sample. Such techniques can be employed by, for example, a pathologist analyzing a tissue sample for particular disease characteristics. Additionally or alternatively, confocal microscopy, fluorescence microscopy, electron microscopy and/or multi-spectral imaging techniques can be used to visualize the sample and/or the bio-specimen standard. Visualization of the bio-specimen standard can be performed by an end user, such as by a sequential or side-by-side comparison of the sample and the standard, or via a previously obtained image provided to the end user, as described above. For example, as shown schematically in FIG. 3, the bio-specimen standard 302 can be mounted on a common substrate 300 (e.g., a microscope slide) with a sample 304 for microscopic comparison by a pathologist. A healthy or diseased tissue sample (not shown) can also be mounted on the common substrate 300 for comparison with the sample 304.

In addition to or instead of visually comparing the sample and the standard, the end user can compare the sample to a normal tissue, for example, as part of a disease diagnosis. Since the particular cell line or mixture of cell lines of the bio-specimen standard may have a different morphology than naturally occurring tissue, comparing the sample with normal tissue can be advantageous in certain pathology applications. The standard can also be used to confirm that assays performed in the laboratory are operating within defined tolerances.

In addition, the bio-specimen standard can be used to determine the protein composition of the sample. In embodiments, the bio-specimen standard can be mixed with the sample and evaluated using mass spectrometry. Since components of the bio-specimen standard have been labeled using minor stable isotopes, the mass spectrometry data of the mixed standard and sample can be used to quantify the corresponding unlabeled components in the sample. Other protein evaluation techniques can be used as well. For example, the protein composition of the sample can be determined from comparison with the standard using an H&E stains, IHC, IF, and/or mass spectrometry assays. Such mass spectrometry assays can include, but are not limited to, electrospray ionization (ESI), laser ablation with electrospray ionization (LAESI) and matrix-assisted laser desorption ionization (MALDI) imaging.

Multiple bio-specimen standards can be incorporated into a tissue microarray. The multiple bio-specimen standards can be a range of cell culture types and/or conditions and/or dilutions. For example, a set of bio-specimen standards, each representing a distinct breast cancer cell line, can be arrayed. The constituents of these standards can assist in proper classification of a breast cancer specimen. Additionally, these standards can be grown under different conditions known to produce different levels of protein expression which have been previously characterized. This growth under different conditions can be done to permit detection of certain proteins which, under other growth conditions, would be below the limits of detection of the assay. Additionally or alternatively, the growth under different conditions can be performed so as to generate expression of modified states of proteins, such as splice variants of certain proteins or post-translationally modified proteins. For example, protein phosphorylation can be an important regulatory mechanism. Growing cells under conditions known to result in phosphorylation of a certain protein or proteins may permit assay of these proteins in their phosphorylated state.

Additionally or alternatively, any of the bio-specimen standards can be diluted prior to fixation to produce a dilution series of the standard. This dilution series can then be used to create a calibration curve of a set of molecules for an assay such that the concentrations of these molecules in a subsequently assayed bio-specimen can be determined.

Figure 4:
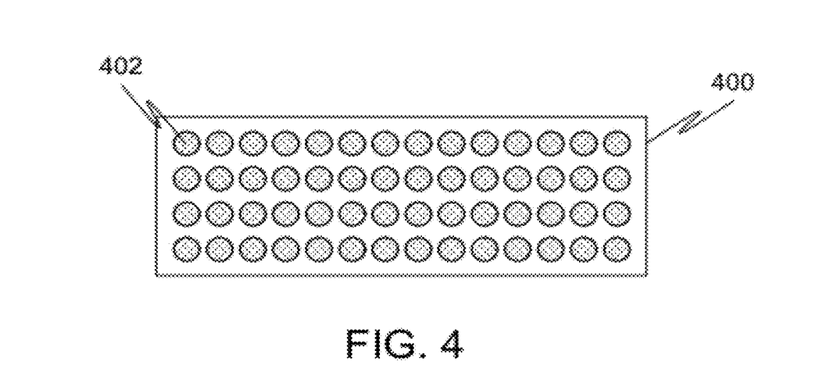
FIG. 4 is a simplified drawing of a plan view of a substrate with a bio-specimen standard array mounted thereon, according to one or more embodiments of the disclosed subject matter.

One or more of the bio-specimen standards can be provided as a respective block or blocks of preserved cell culture. Evaluation of a particular sample may only require a small portion of the block, such that the block can accommodate the evaluation of more than one sample. Thus, characterization in 110 of a block of bio-specimen standard may only be needed once. For example, the block of bio-specimen standard can be sectioned for comparison with a sectioned sample. The sections of the standard and the sample can be substantially the same size or different sizes. The one or more bio-specimen standards can be a different cell culture type, formed by a different processing condition, and/or have a different dilution from each other. Also, the bio-specimen standard can be processed into a tissue microarray along with other bio-specimen standards or bio-specimens. For example, the tissue microarray may take the form of a number of individual spots 402 including cells of different cultures, types, and/or characteristics mounted on a common substrate 400, as shown in FIG. 4. Some of the spots 402 may be reserved for mounting of a sample for side by side comparison with the reference standard cells.

The use of the bio-specimen standard in 114 is not limited to determining the composition of a sample. Rather, in embodiments, one or more of the bio-specimen standards can be used as a type of benchmark to determine certain characteristics of the sample. For example, each bio-specimen standard can serve as a reference for development of a cell culture at various points in time. In other words, a particular cell type can be grown in a medium and preserved at different times during the growing process to form the multiple bio-specimen standards. Visual and/or proteomic analysis and comparison of a sample with the multiple bio-specimen standards can be used to assess similarity with each of the different stages of cell growth.

In embodiments, the multiple bio-specimen standards can also be used to provide a reference for growing cell cultures, i.e., to determine stage of growth of a sample cell culture. Primary cell cultures can be preserved as bio-specimen standards. The expression profiles of primary cell cultures can often change significantly in response to culturing and to varied culture conditions. Bio-specimen standards of the primary cultures can thus be created at different time points and/or under different conditions. Such different conditions can include, but are not limited to, type of growth media, growth temperatures, and type of growth substrates. For example, the growth substrate may be two- or three-dimensional culturing scaffolds. These standards can be used to characterize and assess newly acquired primary cell cultures.

The use of multiple bio-specimen standards can also find application to analysis of disease progression. In embodiments, one or more of the bio-specimen standards can be used as a type of benchmark for a stage of a particular disease. For example, each bio-specimen standard can serve as a reference for development of diseased cells at various stages, such as pre-cancerous, stage I, stage II, etc. Visual and/or proteomic analysis and comparison of a sample with the multiple bio-specimen standards can be used to assess similarity with each of the different stages of the disease and thereby determine a stage of the disease in the sample.

In embodiments, one or more of the bio-specimen standards can be used to determine correlations between other samples. While the expression level of specific proteins or metabolites can be useful in many cases, the overall expression profile of a given type of analyte may also be useful. Overall expression profiles from bio-specimens can be compared to the overall expression profiles of one or more bio-specimen standards. These bio-specimen standards can be chosen to represent a range of cell types, growth conditions, tissue types, disease classification types, etc. Data analysis methods, such as hierarchical clustering, k-means clustering, self-organizing maps and principal component analysis, can be used to determine degrees of similarity between the sample and the standard(s).

The usage herein of "overall expression profile" means the use of more than one analyte to, potentially, all detectable analytes to create a profile. Moreover, as used herein, analyte can be any substance or component to be analyzed, including, but not limited to, any molecular component of a biological cell. Also, an expression value can include measures of protein expression (as determined by means known to those skilled in the art) and/or a measure of expression of group of proteins (such as proteins which are not uniquely identifiable due to varying forms of expression, e.g., splice variants, modifications, or proteins which have been grouped together based on some trait, e.g., trans-membrane helices, gene ontology classification, protein pathway classification, etc.), or combinations of these values.

In embodiments, one or more of the bio-specimen standards can serve as a standard for which proteins are extracted to create reverse phase protein microarrays. Proteins can be extracted from one or more bio-specimen standards using antigen retrieval techniques (heating) or derivatives thereof. These extracts can be spotted onto an appropriate substrate at defined concentrations, so as to create a dilution series. A range of extracts from different bio-specimen standards can be spotted onto the same substrate to create an array representative of a wide range of bio-specimens. Bio-specimen standards can be mixed post-extraction to create novel standards. Bio-specimen standards can be processed post-extraction to isolate components of the standard. For example, the protein constituents can be fractionated by centrifugal, chemical, chromatographic, or electrophoretic methods.

These fractions can then be used alone or in novel combinations for use in reverse phase protein arrays (RPPA). For example, proteins which constitute a known biological pathway can be isolated to varying degrees of purity to allow RPPA analysis specific to this pathway and with higher sensitivity than possible with an unprocessed extract. Alternatively, the protein extracts can be enzymatically processed to generate peptides which can be spotted. The peptides can also be fractionated and spotted or the fractions combined and spotted. Also, the protein extracts can be processed to enrich for proteins with specific properties such as glycoproteins or phosphoproteins. These enriched fractions, and/or the depleted fractions of the bio-specimen standard can be spotted. For example, the RPPA can take the form of a number of individual spots 402 including lysates from cells of different cultures, types, and/or characteristics mounted on a common substrate 400, as shown in FIG. 4. Some of the spots 402 can be reserved for lysates from cells of a sample for side by side comparison with the lysates from the reference standard.

These post-processing methods can be combined in different ways to create novel standards which are derivative of the original(s). For example, proteins from a range of bio-specimen standards produced under different growth conditions can be extracted to represent all possible phosphorylation moieties under those conditions. The extract can then be enriched for phosphoproteins using a metal affinity-based enrichment method and spotted. Alternatively, the extract can be enzymatically processed with an enzyme such as trypsin, and the resulting phosphopeptides enriched using metal affinity-based enrichment methods, which can then be spotted. Alternatively, the enriched phosphopeptides can be fractionated, and the fractions used alone or in combination for spotting.

Glycoproteins can be enriched using lectin-affinity enrichment methods. The enriched glycoproteins can be enzymatically processed to release attached oligosaccharides. These oligosaccharides can be used in a reverse phase oligosaccharide array or may be further processed, such as by fractionation or alternative selection of a subset or subsets, prior to use in an array. Such post-processing serves to create derivatives of the original bio-specimen standard that have specific properties and can permit novel analysis or analyses with improved performance characteristics. However, the post-processing of the bio-specimen standard can include other techniques and be used for other purposes than those disclosed herein. Accordingly, the disclosed techniques and purposes are to be understood as exemplary in nature and not limiting.

Although the above steps of a process for fabricating and/or using the reference standard have been described and illustrated together, it is of course contemplated that one or more steps can be performed separately or together, at the same time or at different times, at the same location or at different locations, and/or in the illustrated order or out of order. Additionally, it is contemplated that one or more steps can be optionally omitted. For example, the formation 108 of the reference standard can be performed by a first user, the characterization 110 of the reference standard can be performed by a second user, and the use 114 can be performed by an end user. In another example, the formation/characterization 112 can be performed together by a first user while the use 114 can be performed by a separate end user. In still another example, all steps can be performed by the end user. In another example, previously labeled cells could be used as the starting point for subsequent preservation 106, characterization 110, and use 114.

Although particular configurations have been discussed herein, other configurations can also be employed. Furthermore, the foregoing descriptions apply, in some cases, to examples generated in a laboratory, but these examples can be extended to production techniques. For example, where quantities and techniques apply to the laboratory examples, they should not be understood as limiting. In addition, although certain materials, chemicals, or components have been described herein, other materials, chemicals (elemental or compositions), or components are also possible according to one or more contemplated embodiments. For example, although formalin has been described as a particular fixative, other fixatives, such as glutaraldehyde, are also possible.

Moreover, although it has been discussed that a cell culture is used for the bio-specimen standard, it will be appreciated that the bio-specimen standard may include a single type of cell line or a mixture of cell line types. Thus, a single bio-specimen standard may include a mixture of different cell types for use as a reference for one or more samples. Selection of the types of cell lines in the standard as well as the minor isotopes for labeling in the standard can be chosen by the skilled artisan based on the type of sample to be analyzed and the proteins desired to be characterized.

These examples and embodiments are not to be understood as limiting. Rather, it is to be understood that the particular methodologies, protocols, cells, chemicals, etc. can be varied and/or modified without departing from the scope of the disclosed subject matter. Features of the disclosed embodiments may be combined, rearranged, omitted, etc., within the scope of the present disclosure to produce additional embodiments. Furthermore, certain features may sometimes be used to advantage without a corresponding use of other features.

It is, thus, apparent that there is provided, in accordance with the present disclosure, minor-stable-isotope-labeled reference standards and methods for the fabrication and use thereof. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicant intends to embrace all such alternatives, modifications, equivalents, and variations that are within the spirit and scope of the present invention.

The invention claimed is:

1. A bio-specimen reference standard method comprising:
   growing one or more cell lines in a medium containing a minor stable isotope therein such that proteins of the one or more cell lines are labeled with said minor isotope;
   characterizing a proteome of the one or more cell lines using the isotope-labeled proteins;
   before or after the characterizing, preserving the one or more cell lines having the proteins labeled with said minor isotope by fixation so as to form a bio-specimen reference standard; and
   after the preserving to form the bio-specimen reference standard:
      comparing a sample to the reference standard, the comparing including at least one of microscope visualization, immunohistochemistry (IHC), immunofluorescence (IF), and hematoxylin and eosin (H&E) staining;
      combining a portion of the sample with a portion of the reference standard; and
      performing mass spectrometry on the combined portions of the sample and the reference standard, the characterized proteome of the one or more cell lines being used to characterize a proteome of the sample,
   wherein the characterizing a proteome of the one or more cell lines is before the performing the mass spectrometry on the combined portions of the sample and the reference standard, and
   the characterizing the proteome of the one or more cell lines includes:
      mixing a portion of the one or more cell lines with known quantities of unlabeled, recombinant proteins or unlabeled, synthetic peptides; and
      performing mass spectrometry on the mixture of the known quantities with the portion of the one or more cell lines.

2. The method of claim 1, wherein the one or more cell lines are multiple cell lines, each with different types of cells or different cell characteristics.

3. The method of claim 2, wherein the multiple cell lines are diseased cells at different stages of development.

4. The method of claim 1, wherein the minor isotope is $^{15}N$ or $^{13}C$.

5. The method of claim 1, wherein the minor isotope is included in metabolites or amino acids in the one or more cell lines.

6. The method of claim 1, wherein the characterizing further includes at least one of spectral counting, immunohistochemistry (IHC), immunofluorescence (IF), and hematoxylin and eosin (H&E) stain.

7. The method of claim 1, wherein the characterizing further includes capturing one or more images of the one or more cell lines using a microscope.

8. The method of claim 7, wherein the microscope is one of a light microscope, a fluorescence microscope, a confocal microscope, and an electron microscope.

9. The method of claim 1, wherein the fixation is at least one of formalin fixation and glutaraldehyde fixation.

10. The method of claim 1, wherein the characterizing is performed on the one or more cell lines after said fixation thereof in the preserving.

11. The method of claim 1, wherein the sample has been preserved by a fixation process that is the same as the fixation in the preserving the one or more cell lines to form the bio-specimen reference standard.

12. The method of claim 1, wherein the fixation is such that the one or more cell lines are preserved for one or more years.

13. A bio-specimen reference standard method comprising:
   growing one or more cell lines in a medium containing a minor stable isotope therein such that proteins of the one or more cell lines are labeled with said minor isotope;
   characterizing a proteome of the one or more cell lines using the isotope-labeled proteins;
   before or after the characterizing, preserving the one or more cell lines having the proteins labeled with said minor isotope by fixation so as to form a bio-specimen reference standard;
   after the preserving to form the bio-specimen reference standard:
      combining a portion of the sample with a portion of the reference standard; and
      performing mass spectrometry on the combined portions of the sample and the reference standard, the characterized proteome of the one or more cell lines being used to characterize a proteome of the sample,
   wherein the preserving further includes embedding the one or more cells in paraffin.

14. The method of claim 13, wherein the characterizing the proteome of the one or more cell lines includes:
   mixing a portion of the one or more cell lines with known quantities of unlabeled, recombinant proteins or unlabeled, synthetic peptides; and
   performing mass spectrometry on the mixture of the known quantities with the portion of the one or more cell lines.

15. A method of using a bio-specimen reference standard, the method comprising:
   performing a pathological comparison of a sample with the reference standard;
   combining a portion of the sample with a portion of the reference standard; and
   determining a proteome of the sample by performing mass spectrometry on the combined portions of the sample and the reference standard,
   wherein the reference standard includes one or more cells lines preserved by a fixation process,
   proteins of the one or more cell lines are labeled by a minor stable isotope of $^{15}N$ or $^{13}C$ such that an amount of the minor isotope in said proteins is greater than an amount of a respective major isotope,
   a proteome of the one or more cell lines of the reference standard being characterized prior to said determining a proteome of the sample,
   the labeled proteins are used in said determining a proteome of the sample, and
   said performing a pathological comparison includes at least one of immunohistochemistry (IHC), immunofluorescence (IF), hematoxylin and eosin (H&E) staining, and imaging the sample and the standard using one of a light microscope, a fluorescence microscope, a confocal microscope, and an electron microscope.

16. The method of claim 15, further comprising, prior to the performing a pathological comparison:
   growing the one or more cell lines in a medium containing the minor stable isotopes so as to label the proteins of the one or more cell lines with said minor isotopes; and
   characterizing a proteome of the one or more cell lines using the isotope-labeled proteins.

17. The method of claim 15, wherein the sample is a tissue sample, and the comparison further includes visually comparing the morphology of the tissue sample to normal tissue.

18. The method of claim 15, wherein:
- the reference standard includes multiple different cells,
- the multiple different cells represent at least one of different times in cell development, different stages of disease progression, different culturing or growth conditions, different cell types, different tissues types, and different disease types,
- said performing a pathological comparison including comparing the sample to the multiple different cells so as to determine a characteristic of the sample, and
- the determined characteristic is at least one of a time of development of the sample, a disease stage of the sample, and a culturing or growth condition of the sample.

19. The method of claim 15, wherein the performing a pathological comparison includes comparing an overall expression profile of the sample for at least one analyte to that of the reference standard using at least one of hierarchical clustering, k-means clustering, self-organized mapping, and principal component analysis.

20. The method of claim 15, wherein the sample and the reference standard are preserved according to the same fixation process.

21. The method of claim 15, wherein the fixation process preserves the one or more cell lines of the reference standard by embedding in paraffin.

22. The method of claim 16, wherein the characterizing the proteome of the one or more cell lines includes:
- mixing a portion of the one or more cell lines with known quantities of unlabeled, recombinant proteins or unlabeled, synthetic peptides; and
- performing mass spectrometry on the mixture of the known quantities with the portion of the one or more cell lines.

* * * * *